United States Patent
Ushio et al.

(10) Patent No.: US 6,504,073 B1
(45) Date of Patent: *Jan. 7, 2003

(54) CATALYST FOR CONVERTING AROMATIC HYDROCARBON COMPOUND AND METHOD OF CONVERTING AROMATIC HYDROCRABON COMPOUND

(75) Inventors: Masaru Ushio, Yokohama (JP); Eiji Yasui, Yokohama (JP); Fumio Haga, Yokohama (JP); Toshiyuki Enomoto, Yokohama (JP)

(73) Assignee: Nippon Mitsubishi Oil Corporation (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/146,165

(22) Filed: Jul. 20, 1998

Related U.S. Application Data (62) Division of application No. 08/651,518, filed on May 22, 1996, now abandoned.

(30) Foreign Application Priority Data

May 20, 1995 (JP) .............................................. 7-150980
Dec. 1, 1995 (JP) .............................................. 7-335654

(51) Int. Cl.$^7$ ................................................ C07C 5/52
(52) U.S. Cl. ..................... 585/475; 585/470; 208/134; 208/135; 208/136; 208/137; 208/138
(58) Field of Search .................. 208/134, 135, 136, 137, 138; 585/470, 475

(56) References Cited

U.S. PATENT DOCUMENTS

| | | | | |
|---|---|---|---|---|
| 3,476,821 A | * | 11/1969 | Brandenburg et al. | 585/475 |
| 3,780,122 A | * | 12/1973 | Pollitzer et al. | 585/474 |
| 3,912,659 A | * | 10/1975 | Brandenburg et al. | 502/66 |
| 4,501,656 A | * | 2/1985 | Dufresne et al. | 208/111 |
| 4,912,073 A | * | 3/1990 | Chu | 502/85 |
| 5,030,787 A | * | 7/1991 | Absil et al. | 585/475 |
| 5,198,595 A | * | 3/1993 | Lee et al. | 585/467 |
| 5,202,516 A | * | 4/1993 | Lee et al. | 585/467 |
| 5,243,116 A | * | 9/1993 | Lee et al. | 585/467 |
| 5,321,183 A | * | 6/1994 | Chang et al. | 585/475 |
| 5,336,824 A | * | 8/1994 | Shamshoum et al. | 585/475 |
| 5,367,099 A | * | 11/1994 | Beck et al. | 585/475 |
| 5,763,720 A | * | 6/1998 | Buchanan et al. | 585/475 |
| 5,800,698 A | * | 9/1998 | Tejada et al. | 208/216 R |
| 5,804,059 A | * | 9/1998 | Wu et al. | 208/135 |
| 5,817,903 A | * | 10/1998 | Wu et al. | 585/486 |
| 5,847,256 A | * | 12/1998 | Ichioka et al. | 585/470 |
| 5,866,742 A | * | 2/1999 | Wu et al. | 585/475 |
| 5,866,744 A | * | 2/1999 | Wu et al. | 585/486 |
| 5,952,536 A | * | 9/1999 | Nacamuli et al. | 585/475 |

* cited by examiner

*Primary Examiner*—Nadine G. Norton
(74) *Attorney, Agent, or Firm*—Ostrolenk, Faber, Gerb & Soffen, LLP (57) ABSTRACT

A method for converting benzene and aromatic hydrocarbon compounds having 9 or more carbon atoms contained in a material oil having a boiling point of 30~210° C. into toluene and aromatic hydrocarbon compounds having 8 carbon atoms in the presence of hydrogen and the said catalyst. The catalyst can be obtained by carrying at least one metal or metal compound selected from Group VIII and Group VIA of the Periodic Table on a carrier containing zeolites in which maximum diameter among diameters of its micropores is 0.6–1.0 nm and a ratio of $SiO_2/Al_2O_3$ is 50 or more.

17 Claims, 1 Drawing Sheet

CATALYST FOR CONVERTING AROMATIC HYDROCARBON COMPOUND AND METHOD OF CONVERTING AROMATIC HYDROCRABON COMPOUND

This is a division of application Ser. No. 08/651,518, filed May 22, 1996, now abandoned.

BACKGROUND OF THE INVENTION

1. Field of the Invention

This invention relates to a catalyst for the conversion of aromatic hydrocarbon compounds, and more specifically relates to a catalyst for the conversion into toluene and aromatic hydrocarbon compounds having 8 carbon atoms, a more useful gasoline base, by reacting benzene with aromatic hydrocarbon compounds having 9 or more carbon atoms.

This invention further relates to a method of converting aromatic hydrocarbon compounds, and more specifically relates to a method of converting aromatic hydrocarbon compounds into toluene and aromatic hydrocarbon compounds having 8 carbon atoms, a more useful gasoline base, by reacting benzene with aromatic hydrocarbon compounds having 9 or more carbon atoms.

2. Background Art

Aromatic hydrocarbon compounds contained in a gasoline base generally have higher octane values, and are superior as a gasoline base because of their high calorific value. Among them, toluene and aromatic hydrocarbon compounds having 8 carbon atoms especially have higher octane values and drive-ability levels, and thus their contents are desirable to be increased. In particular, methods of directly converting benzene and aromatic hydrocarbon compounds having 9 or more carbon atoms in the gasoline fraction into toluene and aromatic hydrocarbon compounds having 8 carbon atoms are significantly meaningful.

Reactions of aromatic hydrocarbon compounds to convert aromatic hydrocarbon compounds having different carbon atoms include the transalkylation reaction and the disproportionation reaction. The transalkylation reaction allows a reactant to react with plural different aromatic hydrocarbon compounds, while the disproportionation reaction of aromatic hydrocarbon compounds is a reaction between the same aromatic hydrocarbon compounds with two molecules.

A well known process regarding these reactions is the manufacture of benzene and xylene utilizing the disproportionation reaction of toluene. Further, as an application of this reaction, there also exists a method of increasing xylene yields through inducing transalkylation by adding aromatic hydrocarbon compounds having 9 or more carbon atoms into the starting materials.

However, this process does not require benzene as a starting material, but requires toluene which itself is useful as a gasoline base. In addition, highly purified materials are used in this process because it is designed to synthesize chemical industrial starting materials, and thus no particular attention has been paid to gasoline fractions, etc. which are mixtures of other compounds, namely various kinds of hydrocarbon compounds including aliphatic hydrocarbon compounds.

The U.S. Pat. No. 5,347,061 discloses a method of directly converting benzene and aromatic hydrocarbon compounds having 9 or more carbon atoms in the gasoline fraction into toluene and aromatic hydrocarbon compounds having 8 carbon atoms. The disclosed method is a process of manufacturing toluene and aromatic hydrocarbon compounds having 8 carbon atoms by inducing transalkylation, alkylation and decomposition of the fractions of hydrocarbon compounds with 6 carbon atoms which is rich in benzene and obtained by distilling reformed gasoline and the fractions of mixture of a aromatic hydrocarbon compounds with 9 or more carbons and non-aromatic hydrocarbon compounds in the presence of acidic metalosilicate catalyst. As for the acidic metarosilicate catalysts, there is disclosed zeolite catalysts such as ZSM-5 as preferable compounds, but no detailed description with regard to diameters of micropores of the carrier or carrying a metal on a carrier has been made.

It is an object of the present invention to provide a catalyst having a high activity and selectivity with less deactivation and suitably used for converting compounds comprising benzene and aromatic hydrocarbon compounds having 9 or more carbon atoms into toluene and aromatic hydrocarbon compounds having 8 carbon atoms, which is a more useful gasoline base.

It is another object of the present invention to provide a method of converting compounds comprising benzene and aromatic hydrocarbon compounds having 9 or more carbon atoms into toluene and aromatic hydrocarbon compounds having 8 carbon atoms, a more useful gasoline base.

SUMMARY OF THE INVENTION

As a result of elaborate efforts by the inventors to develop a novel catalyst to be used for direct conversion into toluene and aromatic hydrocarbon compounds having 8 carbon atoms as a more useful gasoline base by allowing benzene to react with aromatic hydrocarbon compounds having 9 or more carbon atoms, they have successfully found that a catalyst having a specific metal carried on a carrier containing zeolites with a large maximum diameter of the micropores and a large ratio of $SiO_2$ to $Al_2O_3$ has a high activity and a excellent selectivity with less deactivation when it is used with a material oil having a specific range of a boiling point.

According to one aspect of the present invention, there is provided a catalyst for converting benzene and aromatic hydrocarbon compounds having 9 or more carbon atoms contained in a material oil having a boiling point of 30~210° C. into toluene and aromatic hydrocarbon compounds having 8 carbon atoms in the presence of hydrogen, said catalyst being obtained by allowing a carrier containing zeolites in which the maximum diameter among diameters of its micropores is 0.6~1 nm and the ratio of $SiO_2/Al_2O_3$ is 50 or more to carry at least one kind of metal or its compounds, the metal being selected from Group VIII and Group VIA of the Periodic Table.

According to the second aspect of the present invention, there is provided a method of converting benzene and aromatic hydrocarbon compounds having 9 or more carbon atoms contained in a material oil having a boiling point of 30~210° C. into toluene and aromatic hydrocarbon compounds having 8 carbon atoms in the presence of hydrogen and a catalyst obtained by allowing a carrier containing zeolites in which the maximum diameter among diameters of its micropores is 0.6~1 nm and the ratio of $SiO_2/Al_2O_3$ is 50 or more to carry at least one kind of metal or its compounds, the metal being elected from Group VIII and Group VIA of the Periodic Table.

Hereinafter the present invention will be more particularly described along with the accompanying drawings.

DETAILED DESCRIPTION OF THE PREFERRED EMBODIMENTS

The catalyst according to the present invention is characterized in that said catalyst can be obtained by allowing a carrier containing zeolites in which the maximum diameter among diameters of its micropores is 0.6~1 nm and the ratio of $SiO_2/Al_2O_3$ is 50 or more to carry at least one kind of metal or its compounds, the metal being selected from Group VIII and Group VIA of the Periodic Table.

The microporous structures of the materials for porous catalysts are generally classified into flow route, macropore (porous diameter exceeding 50 nm), mesopore (porous diameter ranging from 2 to 50 nm), micropore (porous diameter less than 2 nm). The porous catalysts include the materials having 2 or more different sized micropores, and in the present invention the maximum diameter among diameters of its micropores is the largest entrance diameter among the diameters of all pores and needs to be 0.6~1.0 nm. Such a micropore is usually comprised of twelve-membered ring of oxygen atoms forming an entrance of the micropore. In the present invention, when micropore is not a round, but an ellipse, a major axis thereof is referred to as a microporous diameter.

The maximum diameter, among diameters of micropores of zeolite to be used in the present invention needs to be 0.6~1.0 nm, preferably 0.6~0.8 nm. When it is less than 0.6 nm, it is undesirable since the reaction activity in the conversion from benzene and aromatic hydrocarbon compounds having 9 or more carbon atoms into toluene and aromatic hydrocarbon compounds having 8 carbon atoms is decreased and the selectivity of decomposition reactions of fatty hydrocarbon compounds becomes higher.

Zeolites used in the present invention include, for example, mordenite, X-type zeolite, Y-type zeolite, offretite, β-type zeolite, L-type zeolite, Ω-type zeolite. Among them, mordenite and Y-type zeolites are preferred, and more specifically mordenite is preferably used. These zeolites can be either synthesized or natural products. In addition, one or more kinds of zeolites may be used if necessary in the present invention.

The molar ratio of $SiO_2/Al_2O_3$ in zeolites used in the present invention is preferred to be larger in terms of the activity and the deactivation of catalysts and the stability when reactivating catalysts. The ratio of $SiO_2/Al_2O_3$ needs to be 50 or more, preferably 80 or more, more preferably from 100 to 300 and most preferably from 150 to 250. Zeolites having such a large ratio of $SiO_2/Al_2O_3$ may be synthesized, if possible, by appropriately adjusting the ratio to obtain a desired level, but may also be obtained by synthesizing zeolites having a smaller ratio of $SiO_2/Al_2O_3$ and conducting dealuminization by known methods such as steaming. or acid treatment.

In general, zeolite has a negative charge in a crystalline skeleton wherein there exists a counter cation to compensate it. Said counter cation can freely be selected for zeolite in the present invention, but preferably is hydrogen ion or a mixture of hydrogen ion and alkali metal ion and/or alkali earth metal ion, more preferably a mixture of hydrogen ion and alkaline metal ion and/or alkaline earth metal ion.

The ratio of hydrogen ion to the entire cation is preferably 20% or higher as an ion equivalent, more preferably 30% or higher and most preferably in a range from 40 to 90%.

The ratio of alkali metal ion and/or alkaline earth metal ion to the entire cation is preferably 80% or lower as an ion equivalent, more preferably 70% or lower and more particularly preferable in a range from 10 to 60%. As a counter cation, $K^+$ and $Na^+$ are preferable among alkaline metal ions while $Mg^{2+}$ and $Ca^{2+}$ are preferable among alkaline earth metal ion.

A zeolite containing the above described alkali metal ion and/or alkaline earth metal ion as a counter cation, can be obtained by exchanging a part of hydrogen ions with an alkali metal ion and/or an alkaline earth metal ion when the counter cations in the material zeolite are mostly hydrogen ions. On the other hand, when the counter cations in the material zeolites are mostly alkali metal ions and/or alkaline earth metal ions, it may be possible to exchange a part of these metal ions with a hydrogen ion or to exchange a part of hydrogen ions with these metal ions again after exchanging almost all of these metal ions with hydrogen ions. When the exchange from the counter ions into hydrogen ions is made, it is possible to take another known method where the counter ions are changed into hydrogen ions by calcination after exchanging into ammonium ions other than the method of directly exchanging into hydrogen ions.

When the catalyst according to the present invention is to be prepared, it may carry metal or the mold may proceeded earlier, but carrier molding is preferred to proceeded earlier than carrying metal. For molding, known molding methods may be used, for example, extrusion molding, tabletting, oil dropping and so on. The extrusion molding method is the most preferable. Binders, whenever necessary, may be used for molding.

Since there is no specific restriction in the binders, any kinds of binders, e.g. metal oxides such as alumina, titania, silica-alumina, or clay minerals can be used. Among them, alumina, silica and clay minerals are preferred and alumina is the most preferable. If necessary, two or more kinds of binders may be used. There is no specific limitation in the amount of the used binder(s), but it is preferably 5~50% by mass on the basis of the total amount of the entire carrier including the binder(s), and more preferably 10~30% by mass. The catalytic performance may be reduced when the binder quantity is excessive for use or the molding may become difficult when the binder quantity is too small.

Metals to be carried with catalysts according to the present invention are at least one kind of metal selected from the group VIII or VIA of the Periodic Table. The metals in the group VIII of the Periodic Table are concretely Co, Fe, Ni, Ru, Rh, Pd, Os, Ir and Pt. Preferably Co, Fe, Ni, Ru, Rh, Pd, Ir and Pt may be used. More preferably Ni, Pd and Ir, and most preferably Ni and Pd may be used.

The metals in the group VIA of the Periodic Table are concretely Cr, Mo and W, preferably Mo and W, and more preferably Mo.

Each of these metals may be used alone or the metals of more than 2 kinds may be combined in use.

Since there is no specific limitation in the method of carrying metals, conventional carrying methods may be applied. For example, impregnation method, CVD (Chemical Vapor Deposition) method, etc. may be included. Among them, preferably the impregnation method may be used. In the impregnation method, adsorption method, ion exchange method, vaporizing-drying method, incipient wetness method and spraying method are more preferable in particular.

Starting materials for the metals to be carried may be those that are conventionally employed. For example, metal chloride, nitrate, sulfate, etc. may be quoted. In addition, amine complexes such as $Pd(NH_3)_4Cl_2$ and $Pd(NH_3)_4(NO_3)_2$ can also be used.

As for catalysts to be used in the present invention, the metals may be carried as metal atoms or as the compounds such as sulfide, oxide, etc., but it is more preferable to carry the metals as metal atoms or their sulfides in terms of the reaction activity.

Since the catalysts according to the present invention are catalysts in which at least one kind of metals selected from the group VIII or VIA of the Periodic Table on the aforementioned catalysts, it is undesirable that metal is used without any carrier as the catalyst because the initial catalytic activity may be reduced and/or the catalyst may easily deactivate.

There is no specific limitation in the quantity of a used metal to be carried as the appropriate amount thereof is selected in accordance with the kind of metal and reaction conditions, etc., but the metal is preferably used in an amount of 0.01~5% by mass in case of using Ru, Rh, Pd, Os, Ir and Pt, more preferably in an amount of 0.05~3% by mass and most preferable in an amount of 0.1~1% by mass as converted into metals themselves on the basis of the total amount of the entire catalyst including the metals. As for Co, Fe, Ni, Cr, Mo and W, they are preferable in an amount of 0.1~15% by mass, more preferable in an amount of 0.3~10% by mass, and most preferable in an amount of 0.5~5% by mass.

The catalyst according to the present invention is desirably calcinated after its preparation. The calcination temperature is 200~600° C. in general and more preferably 300~500° C. It is desirable to carry out either reduction or sulfurization pretreatment prior to the start of reaction.

Hydrogen-reduction using a gas containing hydrogen is desirable for such a reduction treatment, and the reduction temperature is generally 100~600° C., and preferably 200~500° C. Sulfurization treatment is desirable by using sulfurization agents such as hydrogen sulfide, carbon disulfide, dimethyl disulfide (DMDS), etc. in the presence of a gas containing hydrogen gas. The sulfurization temperature is preferably 100~500° C. and more preferably 200~400° C.

When the catalyst according to the present invention is used, hydrogenation of aromatic rings, i.e. a side reaction, normally seldom occurs. However, since this side reaction may become extremely stronger depending on the kinds of metal, reaction conditions, etc., it is desirable to carry a sulfurization pretreatment.

In the present invention, the above-mentioned catalyst is used for the conversion of benzene and aromatic hydrocarbon compounds having 9 or more carbon atoms contained in the material oil having a boiling point of 30~210° C. into toluene and aromatic hydrocarbon compounds having 8 carbon atoms.

The material oil employed in the present invention may be a material oil having a boiling point of 30~210° C. according to the measurement method specified by ASTM D86, preferably 30~200° C. and more preferably 30~195° C. Oil having a boiling point of more than 210° C. is not recommended since coking is apt to develop and thereby adversely affect a catalytic life.

In addition to the above, the material oil to be used for the present invention is required to contain benzene and aromatic hydrocarbon compounds having 9 or more carbon atoms. The amount of benzene and aromatic hydrocarbon compounds having 9 or more carbon atoms contained in the material oil may be freely decided, but more the amount is better in both cases in terms of reaction efficiency. In the present invention, the content of benzene is 1% by mass or more on the basis of the total amount of the entire material oil, preferably 5% by mass or more, and more preferably 10% by mass or more. Further, in the present invention the content of aromatic hydrocarbon compounds having 9 or more carbon atoms is preferably 1% by mass or more on the basis of the total amount of the material oil, preferably 30% by mass or more, and more preferably 50% by mass or more.

The ratio between benzene and aromatic hydrocarbon compounds having 9 or more carbon atoms in the material oil (the molar ratio of aromatic hydrocarbon compounds having 9 or more carbon atoms/benzene) is preferably 0.5~10, and more preferably 1~5. When the molar ratio is too small, the conversion ratio of benzene may be reduced. When the molar ratio is too large, the conversion ratio of aromatic hydrocarbon compounds having 9 or more carbon atoms becomes lower and less efficient.

The material oil to be used for the present invention that meets the above requirements which are specific ranges of boiling points and to contain benzene and aromatic hydrocarbon compounds having 9 or more carbon atoms may be freely selected.

The above material oil may be a pure product such as a chemical industrial material, but the material oil to be used for the present invention may be mixture with other compounds, more concretely, petroleum fractions, for example, that can be obtained by distilling crude oil, or petroleum fractions treated with various kinds of procedures. Among them, reformed gasoline obtained by a catalytic reforming apparatus, fluidized bed catalytic cracking gasoline that can be obtained by a fluidized bed catalytic cracking apparatus may be used, and reformed gasoline rich in aromatic components is favorably used in particular.

The above-mentioned mixture generally contains toluene and aromatic hydrocarbon compounds having 8 carbon atoms, namely a reaction product associating with the present invention. In the present invention, the mixture oil containing these compounds may be used as the material oil, but it is desirable to use it as the material oil after removing these useful compounds by distillation, etc. in terms of the reaction efficiency. In other words, it is desirable to separate the mixture oil into fractions containing benzene, fractions containing toluene and aromatic hydrocarbon compounds having 8 carbon atoms, fractions containing aromatic hydrocarbon compounds having 9 or more carbon atoms by distilling reformed gasoline or the like, and therafter mixing the fractions containing benzene and aromatic hydrocarbon compounds having 9 or more carbon atoms to obtain the material oil. Further, the fractions containing toluene and aromatic hydrocarbon compounds having 8 carbon atoms may be used as a gasoline base or may also be used as the materials for chemical industry.

When necessary, by the known method such as sulforan extraction, highly purified benzene may further be separated from the distilled fractions containing benzene so as to prepare the material oil by mixing it with the fractions containing aromatic hydrocarbon compounds having 9 or more carbon atoms.

When the conversion reaction of aromatic hydrocarbon compounds is carried out by using the catalyst according to the present invention, it is necessary to carry it out in the presence of hydrogen. There is no specific limitation in the ratio between hydrogen gas and the material oil (volume of hydrogen gas in a normal state of 1 atom and 0° C. volume of the material oil), but it is preferably 50~2000 Nm$^3$/m$^3$, more specifically 500~1500 Nm$^3$/m$^3$. When the ratio between hydrogen gas and the material oil is too small, the catalytic life becomes extremely shorter. On the other hand, it is not economically worse when the ratio between hydrogen gas and the material oil is too large.

The catalyst according to the present invention should be used in the presence of hydrogen, and other reaction conditions can be appropriately selected by the activity of catalysts, compositions of the material oil and productive oil. In addition, there is no specific limitation in the reaction pressure, the reaction temperature, or the liquid hourly space velocity (LHSV).

However, the reaction pressure may be generally in a range of 0.1~6 MPa, and preferably in a range of 2~4 MPa.

The reaction temperature may be generally in a range of 200~550° C., preferably of 250~500° C., and more preferably of 350~500° C. When the reaction temperature is too low, the conversion may be decreased, while the conversion may be also decreased because of preferentially occurring dealkylation when the reaction temperature is too high.

The LHSV is preferably in a range of 0.1~10 h$^{-1}$, and more preferably of from 0.5~5 h$^{-1}$.

Although the reactors in the present invention can be any one of the fixed bed, fluidized bed or expansion bed types, preferably the fixed bed type. The contacting method of the material oil with hydrogen and catalyst may be any one of the methods of parallel elevation flow, parallel descending flow and countercurrent flow. Also, either the flow method or batch method may be acceptable, but the flow method is preferable.

When benzene and aromatic hydrocarbon compounds having 9 or more carbon atoms are converted into toluene and aromatic hydrocarbon compounds having 8 carbons in accordance with the present invention, the conversion ratio is higher with smaller contents of non-reacted benzene and aromatic hydrocarbon compounds having 9 or more carbon atoms in the product oil. Thus, although it is not necessary to mix the product oil with the material oil to repeatedly treat the product oil, recycling the prepared oil as the material oil may be done in order to raise the reaction efficiency.

When recycling is to be done, a part of the prepared oil may be mixed with the material oil or mixed with the material oil after removing the specific fractions of the prepared oil by distillation. It is undesirable to carry out recycling when the benzene concentration in the prepared oil is lower since the recycling of the fractions containing benzene accelerate decomposition of coexisting fatty hydrocarbon compounds having 6 or 7 carbon atoms into light gas oil having less values while thereby reducing the yield of the necessary gasoline base.

Next, the present invention will be explained with the attached drawings, especially a simple embodiment of the process of recycling by use of the catalyst according to the present invention will be explained.

Figure 1:
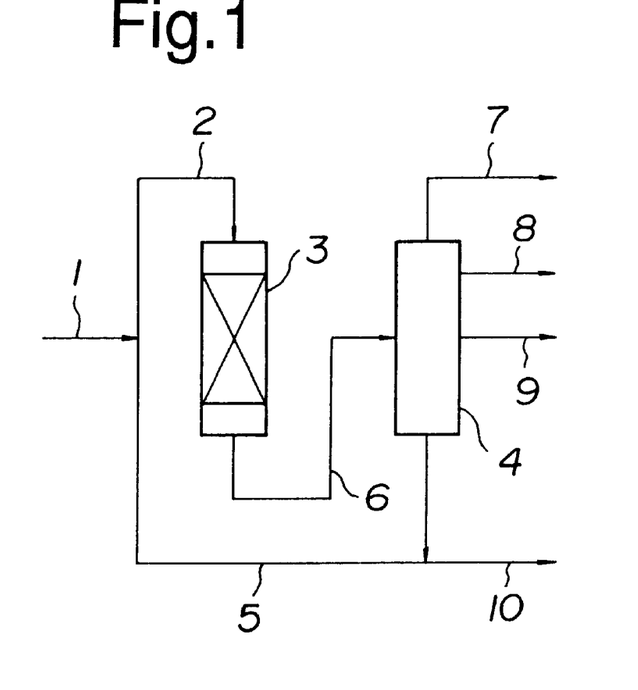
FIG. 1 is a schematic diagram of an embodiment of a process of manufacturing a gasoline base by using the catalyst according to the present invention.

In FIG. 1, a material oil containing benzene and aromatic hydrocarbon compounds having 9 or more carbon atoms is supplied from a conduit (1) to conduit (2) and transferred from conduit (2) to a reactor (3) together with fractions containing aromatic hydrocarbon compounds having 9 or more carbon atoms recycled from a distilling tower (4) via a conduit (5). The prepared oil is transferred to the distilling tower (4) via a conduit (6), and gaseous contents, the fractions containing benzene, the fractions containing toluene and aromatic hydrocarbon compounds having 8 carbon atoms, and the fractions containing aromatic hydrocarbon compounds having 9 or more carbon atoms are separated and transferred conduits (7), (8), (9), and (10), respectively, while at least a part of the fractions containing aromatic hydrocarbon compounds of 9 or more carbon atoms is recycled conduit (5).

Figure 2:
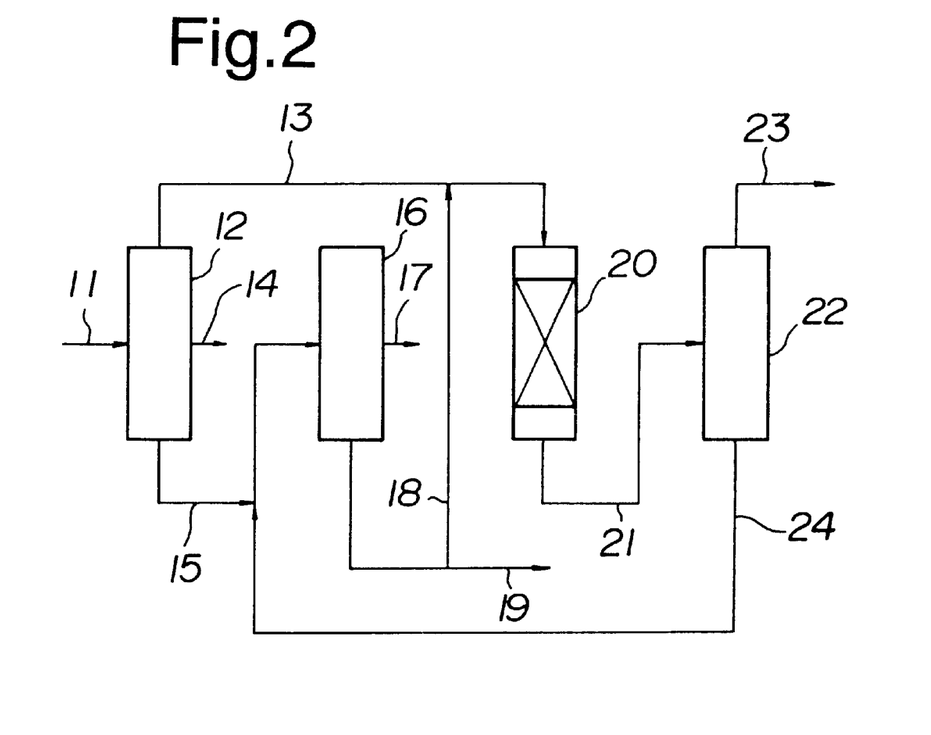
FIG. 2 is a schematic diagram of another embodiment of a process of manufacturing a gasoline base by using the catalyst according to the present invention.

Next, the present invention will be illustrated by FIG. 2 showing another preferred embodiment of a process of recycling by use of the catalyst according to the present invention.

The material oil supplied from a conduit (11) is separated in a distilling tower (12) into fractions containing benzene (into a conduit 13), fractions containing toluene (into a conduit 14), and fractions containing aromatic hydrocarbon compounds having 8 or more carbon atoms (into a conduit 15). After the fractions containing aromatic hydrocarbon compounds having 8 carbon atoms are separated (via a conduit 17) in a distilling tower (16) from the fractions containing aromatic hydrocarbon compounds 8 or more carbon atoms (from the conduit 15 and a conduit 24), at least a part (via a conduit 18) of the fractions (the balance being in a conduit 19) containing aromatic hydrocarbon compounds having 9 or more carbon atoms is transferred to a reactor (20) together with the fractions containing benzene (from conduit 13). The fractions containing benzene and toluene are separated (from a conduit 23) by a distilling tower (22) from the prepared oil (from a column 21) and the fractions containing aromatic hydrocarbon compounds having 8 carbon atoms (into a conduit 24) are transferred to the distilling tower (16).

EMBODIMENT

The examples and comparative examples will be more concretely illustrated, but not limited to these embodiments.

EXAMPLE 1

To hydrogen-ion-type mordenite (No. HSZ690HOA, obtained from Toso K.K.) in which the ratio of SiO$_2$/Al$_2$O$_3$ is 203 and the maximum diameter among diameters of its micropores is 0.70 nm, boehmite defloculated with dilute nitrate was added, and the mixture was kneaded, extrusion molded, dried and calcinated to prepare a carrier for a catalyst. The amount of boehmite was adjusted so that the amount of alumina binder could be 30% by mass on the basis of the total mass of the carrier. Ni of 3% by mass (as metal on the basis of the total mass of the prepared catalyst) on this carrier in a form of an aqueous solution of nickel nitrate by the Incipient Wetness method, and the carrier was dried and calcinated to prepare a catalyst. Next, prior to the following reaction, a sulfurization treatment was conducted using hydrogen gas containing 1% by volume of hydrogen sulfide.

Reaction experiment was conducted on the material oil having the properties and compositions shown in Table 1 by utilizing a pressurized distribution type reaction apparatus having a volume of 20 ml. The material oil was obtained by mixing benzene with the fractions which are separated by distilling reformed gasoline obtained by a catalytic reforming apparatus, have a boiling point of 150~190° C. and mainly contain aromatic hydrocarbon compounds having 9 carbon atoms.

The reaction was conducted under the conditions of a pressure of 3.0 MPa, temperature of 390° C., LHSV of 1.5h$^{-1}$, ratio of hydrogen gas/oil of 800 Nm$^3$/m$^3$, and molar ratio of aromatic hydrocarbon compounds having 9 or more carbon atoms/benzene of 1.9. Table 1 shows the reaction results obtained 72 and 360 hours after the start of reactions, respectively.

EXAMPLE 2

The same catalyst preparation and the same reaction experiment as in the Example 1 were repeated except that another material oil obtained by mixing the fractions containing benzene and the fractions containing aromatic hydrocarbon compounds having 9 carbon atoms which were separated by distilling reformed gasoline obtained by a catalytic reforming apparatus was used instead of the material oil of the example 1. Further, the material oil contains a considerable amount of fatty hydrocarbon compounds having 6 and 7 carbon atoms. The molar ratio of aromatic hydrocarbon compounds having 9 or more carbon atoms/benzene was 2.9 and the obtained results are shown in Table 1.

EXAMPLE 3

The same catalyst preparation and the same reaction experiment as in the example 1 were repeated except that a Na-ion exchanged mordenite by the following method was used instead of the hydrogen-ion type mordenite in which the maximum diameter among diameters of micropores was 0.70 nm and a ratio of $SiO_2/Al_2O_3$ was 203 used in the example 1, and the results are shown in Table 2.

Na-ion Exchanging Method

The mordenite used in the example 1 was added to a NaCl aqueous solution, stirred at 90° C. for 14 hrs, filtered and washed with ion-exchanged water. After then, it was dried and calcinated. The ion-exchanged rate was 50%.

EXAMPLE 4

The same catalyst preparation and the same reaction experiment as in the example 1 were repeated except that a hydrogen-ion type ultrastabilized Y-type zeolite (HSZ390HUA, obtained from Toso K.K.) in which the maximum diameter among diameters of micropores was 0.74 nm and the ratio of $SiO_2/Al_2O_3$ was 240 was used instead of the hydrogen-ion type mordenite in which the maximum diameter among diameters of micropores was 0.70 nm and the ratio of $SiO_2/Al_2O_3$ was 203 used in the example 1, and the results are shown in Table 2.

COMPARATIVE EXAMPLE 1

The same catalyst preparation and the same reaction experiment as in the Example 1 were repeated except that another material oil obtained by mixing purified benzene with the fractions containing aromatic hydrocarbon compounds having 9 carbon atoms which had a boiling point of 150~230° C. and were separated by distilling reformed gasoline obtained by a catalytic reforming apparatus was used instead of the material oil of the example 1, and the results are shown in Table 3.

COMPARATIVE EXAMPLE 2

The same catalyst preparation and the same reaction experiment as in the example 1 were repeated except that a hydrogen-ion type ZSM-5 in which the maximum diameter among diameters of micropores was 0.54 nm and the ratio of $SiO_2/Al_2O_3$ was 26 was used instead of the hydrogen-ion type mordenite in which the maximum diameter among diameters of micropores was 0.70 nm and the ratio of $SiO_2/Al_2O_3$ was 203 used in the example 1, and the results are shown in Table 3.

COMPARATIVE EXAMPLE 3

The same catalyst preparation and the same reaction experiment as in the example 2 were repeated except that a hydrogen-ion type ZSM-5 in which the maximum diameter among diameters of micropores was 0.54 nm and the ratio of $SiO_2/Al_2O_3$ was 26 was used instead of the hydrogen-ion type mordenite in the maximum diameter among diameters of micropores was 0.70 nm the ratio of $SiO_2/Al_2O_3$ was 203 used in the example 2, and the results are shown in Table 4.

COMPARATIVE EXAMPLE 4

The same catalyst preparation and the same reaction experiment as in the example 1 were repeated except that a hydrogen-ion type mordenite (HSZ640HOA, obtained from Toso K.K.) in the maximum diameter among diameters of micropores was 0.70 nm and the ratio of $SiO_2/Al_2O_3$ was 20 was used instead of the hydrogen-ion type mordenite in which the maximum diameter among diameters of micropores was 0.70 nm and the ratio of $SiO_2/Al_2O_3$ was 203 used in the example 1, and the results are shown in Table 4.

COMPARATIVE EXAMPLE 5

The same catalyst preparation and the same reaction experiment as in the example 1 were repeated except that a hydrogen-ion type ultrastabilized Y-type zeolite (HSZ370HUA, obtained from Toso K.K.) in which the maximum diameter among diameters of micropores was 0.74 nm and the ratio of $SiO_2/Al_2O_3$ was 26 was used instead of the hydrogen-ion type mordenite in which the maximum diameter among diameters of micropores was 0.70 nm and ratio of $SiO_2/Al_2O_3$ was 203 used in the example 1, and the results are shown in Table 5.

COMPARATIVE EXAMPLE 6

The same reaction experiment was repeated except that a catalyst which did not comprise any metal on the same carrier as in the example 1 was used instead of the catalyst used in example 1, and the results are shown in Table 5.

TABLE 1

|  | Example 1 | | | Example 2 | | |
| --- | --- | --- | --- | --- | --- | --- |
| Running Time (hours) | Material Oil | 72 | 360 | Material Oil | 72 | 360 |
| CATALYST | Mordenite | | | Mordenite | | |
| Molar Ratio of Silica/Alumina | 203 | | | 203 | | |
| Na-ion Exchanged | None | | | None | | |
| Ni amount to be carried (% by mass) | 3 | | | 3 | | |
| Reaction Pressure (MPa) |  | 3.0 | 3.0 |  | 3.0 | 3.0 |
| Reaction Temperature (° C.) |  | 390 | 390 |  | 390 | 390 |

TABLE 1-continued

|  | Example 1 | | | Example 2 | | |
|---|---|---|---|---|---|---|
| Running Time (hours) | Material Oil | 72 | 360 | Material Oil | 72 | 360 |
| LHSV |  | 1.5 | 1.5 |  | 1.5 | 1.5 |
| $H_2$/Oil Ratio ($Nm^3/m^3$) |  | 800 | 800 |  | 800 | 800 |
| Distillation Property (ASTM-D86 method) IBP/10%/30%/50%/70%/90%/EP | 87/87/159/160/ 161/163/190 | | | 65/70/79/160/ 161.5/163/190 | | |
| Methane (% by mass) | 0.0 | 0.0 | 0.0 | 0.0 | 0.1 | 0.1 |
| Ethane | 0.0 | 7.7 | 7.6 | 0.0 | 3.2 | 3.1 |
| Propane | 0.0 | 6.9 | 6.6 | 0.0 | 6.4 | 6.2 |
| Butane | 0.0 | 3.5 | 2.8 | 0.0 | 2.9 | 2.8 |
| Pentane | 0.0 | 1.0 | 0.7 | 0.1 | 0.8 | 0.7 |
| Hexane | 0.0 | 0.4 | 0.3 | 9.6 | 5.7 | 5.6 |
| Heptane | 0.0 | 0.1 | 0.1 | 4.0 | 1.8 | 1.8 |
| Benzene | 24.7 | 10.7 | 11.3 | 15.3 | 7.0 | 7.2 |
| Toluene | 0.0 | 30.7 | 27.9 | 0.0 | 31.2 | 30.0 |
| Aromatic Compounds having 8 carbon atoms | 1.4 | 27.9 | 28.5 | 1.5 | 28.2 | 27.9 |
| Aromatic Compounds having 9 carbon atoms | 71.0 | 9.8 | 12.8 | 66.3 | 10.9 | 12.9 |
| Trimethylbenzene | 49.7 | 8.5 | 10.6 | 43.2 | 8.7 | 9.8 |
| Others | 21.3 | 1.3 | 2.2 | 23.1 | 2.2 | 2.9 |
| Aromatic Compounds having 10 or more carbon atoms | 3.0 | 1.4 | 1.4 | 3.2 | 2.0 | 2.0 |
| Total | 100.0 | 100.0 | 100.0 | 100.0 | 100.0 | 100.0 |
| Conversion Ratio of Benzene (% by mass) |  | 56.5 | 54.3 |  | 54.3 | 52.9 |
| Conversion Ratio of C9 AHC (% by mass) |  | 86.1 | 82.0 |  | 83.6 | 80.9 |
| Trimethylbenzene |  | 82.8 | 78.7 |  | 79.9 | 77.3 |
| Others |  | 93.9 | 89.7 |  | 90.6 | 87.6 |
| Variation of Conversion Ratio of Benzene (%) |  |  | 95.7 |  |  | 97.6 |
| Variation of Conversion Ratio of C9 AHC |  |  | 95.2 |  |  | 96.3 |

TABLE 2

|  | Example 3 | | | Example 4 | | |
|---|---|---|---|---|---|---|
| Running Time (hours) | Material Oil | 72 | 360 | Material Oil | 72 | 360 |
| CATALYST |  | Mordenite | | | Y-type zeolite | |
| Molar Ratio of Silica/Alumina |  | 203 | | | 240 | |
| Na-ion Exchanged |  | 50% | | | None | |
| Ni amount to be carried (% by mass) |  | 3 | | | 3 | |
| Reaction Pressure (MPa) |  | 3.0 | 3.0 |  | 3.0 | 3.0 |
| Reaction Temperature (° C.) |  | 390 | 390 |  | 390 | 390 |
| LHSV |  | 1.5 | 1.5 |  | 1.5 | 1.5 |
| $H_2$/Oil Ratio ($Nm^3/m^3$) |  | 800 | 800 |  | 800 | 800 |
| Distillation Property (ASTM-D86 method) IBP/10%/30%/50%/70%/90%/EP | 87/87/159/160/ 161/163/190 | | | 87/87/159/160/ 161/163/190 | | |
| Methane (% by mass) | 0.0 | 0.1 | 0.0 | 0.0 | 0.0 | 0.0 |
| Ethane | 0.0 | 7.4 | 7.6 | 0.0 | 8.1 | 7.7 |
| Propane | 0.0 | 6.2 | 5.7 | 0.0 | 6.6 | 5.7 |
| Butane | 0.0 | 3.0 | 2.1 | 0.0 | 4.4 | 4.2 |
| Pentane | 0.0 | 0.9 | 0.6 | 0.0 | 1.3 | 0.6 |
| Hexane | 0.0 | 0.5 | 0.3 | 0.0 | 0.6 | 0.9 |
| Heptane | 0.0 | 0.2 | 0.2 | 0.0 | 0.4 | 0.8 |
| Benzene | 24.7 | 10.7 | 10.7 | 24.7 | 12.0 | 12.3 |
| Toluene | 0.0 | 30.6 | 30.3 | 0.0 | 27.0 | 27.0 |
| Aromatic Compounds having 8 carbon atoms | 1.4 | 28.5 | 29.5 | 1.4 | 29.1 | 27.5 |
| Aromatic Compounds having 9 carbon atoms | 71.0 | 10.4 | 11.3 | 71.0 | 4.9 | 8.6 |
| Trimethylbenzene | 49.7 | 8.7 | 9.3 | 49.7 | 2.2 | 4.8 |
| Others | 21.3 | 1.7 | 1.9 | 21.3 | 2.7 | 3.8 |
| Aromatic Compounds having 10 or more carbon atoms | 3.0 | 1.6 | 1.8 | 3.0 | 5.6 | 4.7 |
| Total | 100.0 | 100.0 | 100.0 | 100.0 | 100.0 | 100.0 |
| Conversion Ratio of Benzene (% by mass) |  | 56.8 | 56.6 |  | 51.3 | 50.0 |
| Conversion Ratio of C9 AHC (% by mass) |  | 85.3 | 84.1 |  | 93.1 | 87.9 |
| Trimethylbenzene |  | 82.4 | 81.2 |  | 95.5 | 90.4 |
| Others |  | 92.1 | 90.9 |  | 87.3 | 82.2 |
| Variation of Conversion Ratio of Benzene (%) |  |  | 99.7 |  |  | 97.4 |
| Variation of Conversion Ratio of C9 AHC |  |  | 98.6 |  |  | 94.5 |

TABLE 3

|  | Comparative Example 1 | | | Comparative Example 2 | | |
|---|---|---|---|---|---|---|
| Running Time (hours) | Material Oil | 72 | 360 | Material Oil | 72 | 360 |
| CATALYST | Mordenite | | | ZSM-5 | | |
| Molar Ratio of Silica/Alumina | 203 | | | 26 | | |
| Na-ion Exchanged | None | | | None | | |
| Ni amount to be carried (% by mass) | 3 | | | 3 | | |
| Reaction Pressure (MPa) | | 3.0 | 3.0 | | 3.0 | 3.0 |
| Reaction Temperature (° C.) | | 390 | 390 | | 390 | 390 |
| LHSV | | 1.5 | 1.5 | | 1.5 | 1.5 |
| $H_2$/Oil Ratio ($Nm^3/m^3$) | | 800 | 800 | | 800 | 800 |
| Distillation Property (ASTM-D86 method) IBP/10%/30%/50%/70%/90%/EP | 87/87/163/164/ 167/180/230 | | | 87/87/159/160/ 161/163/190 | | |
| Methane (% by mass) | 0.0 | 0.0 | 0.0 | 0.0 | 0.3 | 0.3 |
| Ethane | 0.0 | 3.2 | 2.8 | 0.0 | 8.0 | 7.9 |
| Propane | 0.0 | 7.1 | 5.5 | 0.0 | 7.0 | 6.6 |
| Butane | 0.0 | 3.6 | 2.2 | 0.0 | 2.7 | 2.2 |
| Pentane | 0.0 | 1.0 | 1.0 | 0.0 | 1.2 | 1.1 |
| Hexane | 0.0 | 0.8 | 1.0 | 0.0 | 0.2 | 0.3 |
| Heptane | 0.0 | 0.5 | 0.8 | 0.0 | 0.2 | 0.2 |
| Benzene | 24.9 | 13.5 | 16.2 | 24.7 | 11.0 | 14.9 |
| Toluene | 0.0 | 17.8 | 15.1 | 0.0 | 22.8 | 15.5 |
| Aromatic Compounds having 8 carbon atoms | 0.3 | 19.3 | 15.4 | 1.4 | 14.7 | 13.2 |
| Aromatic Compounds having 9 carbon atoms | 62.5 | 22.5 | 28.8 | 71.0 | 29.7 | 35.3 |
| Trimethylbenzene | 42.4 | 16.6 | 21.1 | 49.7 | 29.3 | 32.6 |
| Others | 20.1 | 6.0 | 7.7 | 21.3 | 0.4 | 2.7 |
| Aromatic Compounds having 10 or more carbon atoms | 12.3 | 10.7 | 11.2 | 3.0 | 2.3 | 2.5 |
| Total | 100.0 | 100.0 | 100.0 | 100.0 | 100.0 | 100.0 |
| Conversion Ratio of Benzene (% by mass) | | 45.8 | 34.8 | | 55.5 | 39.6 |
| Conversion Ratio of C9 AHC (% by mass) | | 64.0 | 54.0 | | 58.2 | 50.3 |
| Trimethylbenzene | | 61.0 | 50.3 | | 41.0 | 34.4 |
| Others | | 70.3 | 61.7 | | 98.3 | 87.5 |
| Variation of Conversion Ratio of Benzene (%) | | | 76.0 | | | 71.3 |
| Variation of Conversion Ratio of C9 AHC | | | 85.7 | | | 86.4 |

TABLE 4

|  | Comparative Example 3 | | | Comparative Example 4 | | |
|---|---|---|---|---|---|---|
| Running Time (hours) | Material Oil | 72 | 360 | Material Oil | 72 | 360 |
| CATALYST | ZSM-5 | | | Mordenite | | |
| Molar Ratio of Silica/Alumina | 26 | | | 20 | | |
| Na-ion Exchanged | None | | | None | | |
| Ni amount to be carried (% by mass) | 3 | | | 3 | | |
| Reaction Pressure (Mpa) | | 3.0 | 3.0 | | 3.0 | 3.0 |
| Reaction Temperature (° C.) | | 390 | 390 | | 390 | 390 |
| LHSV | | 1.5 | 3.5 | | 1.5 | 1.5 |
| $H_2$/Oil Ratio ($Nm^3/m^3$) | | 800 | 800 | | 800 | 800 |
| Distillation Property (ASTM-D86 method) IBP/10%/30%/50%/70%/90%/EP | 65/70/79/160/ 161.5/163/190 | | | 87/87/159/160/ 161/163/190 | | |
| Methane (% by mass) | 0.0 | 0.2 | 0.2 | 0.0 | 0.8 | 0.8 |
| Ethane | 0.0 | 4.2 | 4.1 | 0.0 | 6.3 | 6.3 |
| Propane | 0.0 | 8.7 | 8.3 | 0.0 | 3.8 | 3.6 |
| Butane | 0.0 | 3.4 | 3.0 | 0.0 | 1.7 | 1.5 |
| Pentane | 0.1 | 1.1 | 1.0 | 0.0 | 0.8 | 0.6 |
| Hexane | 9.6 | 2.1 | 2.0 | 0.0 | 0.4 | 0.5 |
| Heptane | 4.0 | 1.1 | 0.9 | 0.0 | 0.2 | 0.3 |
| Benzene | 15.3 | 7.6 | 9.3 | 24.7 | 13.2 | 15.6 |
| Toluene | 0.0 | 27.1 | 23.2 | 0.0 | 21.9 | 17.8 |
| Aromatic Compounds having 8 carbon atoms | 1.5 | 14.3 | 12.7 | 1.4 | 17.4 | 15.1 |
| Aromatic Compounds having 9 carbon atoms | 66.3 | 27.5 | 32.9 | 71.0 | 30.9 | 35.3 |
| Trimethylbenzene | 43.2 | 26.5 | 30.1 | 49.7 | 27.4 | |
| Others | 23.1 | 1.0 | 2.7 | 21.3 | 3.5 | 4.3 |
| Aromatic Compounds having 10 or more carbon atoms | 3.2 | 2.5 | 2.6 | 3.0 | 2.6 | 2.7 |
| Total | 100.0 | 100.0 | 100.0 | 100.0 | 100.0 | |
| Conversion Ratio of Benzene (% by mass) | | 50.3 | 39.2 | | 46.5 | 36.5 |
| Conversion Ratio of C9 AHC (% by mass) | | 58.5 | 50.4 | | 56.5 | 50.3 |
| Trimethylbenzene | | 38.7 | 30.3 | | 44.9 | 37.6 |
| Others | | 95.6 | 88.1 | | 83.6 | 79.8 |
| Variation of Conversion Ratio of Benzene (%) | | | 77.9 | | | 78.7 |
| Variation of Conversion Ratio of C9 AHC | | | 86.2 | | | 89.0 |

TABLE 5

|  | Comparative Example 5 | | | Comparative Example 6 | | |
| --- | --- | --- | --- | --- | --- | --- |
| Running Time | Material Oil | 72 | 360 | Material Oil | 72 | 360 |
| CATALYST | Y-type Zeolite | | | Mordenite | | |
| Molar Ratio of Silica/Alumina | 26 | | | 203 | | |
| Na-ion Exchanged | None | | | None | | |
| Ni amount to be carried (% by mass) | 3 | | | None | | |
| Reaction Pressure (MPa) |  | 3.0 | 3.0 |  | 3.0 | 3.0 |
| Reaction Temperature (° C.) |  | 390 | 390 |  | 390 | 390 |
| LHSV |  | 1.5 | 1.5 |  | 1.5 | 1.5 |
| H$_2$/Oil Ratio (Nm$^3$/m$^3$) |  | 800 | 800 |  | 800 | 800 |
| Distillation Property (ASTM-D86 method) IBP/10%/30%/50%/70%/90%/EP | 87/87/159/160/ 161/163/190 | | | 87/87/159/160/ 161/163/190 | | |
| Methane (% by mass) | 0.0 | 0.2 | 0.2 | 0.0 | 0.2 | 0.1 |
| Ethane | 0.0 | 6.9 | 6.7 | 0.0 | 6.0 | 5.7 |
| Propane | 0.0 | 4.1 | 3.8 | 0.0 | 5.1 | 4.5 |
| Butane | 0.0 | 2.5 | 2.5 | 0.0 | 1.2 | 1.1 |
| Pentane | 0.0 | 1.1 | 1.1 | 0.0 | 0.3 | 0.3 |
| Hexane | 0.0 | 0.5 | 0.6 | 0.0 | 0.5 | 0.5 |
| Heptane | 0.0 | 0.3 | 0.4 | 0.0 | 0.3 | 0.3 |
| Benzene | 24.7 | 14.3 | 15.6 | 24.7 | 23.9 | 23.9 |
| Toluene | 0.0 | 16.6 | 21.7 | 0.0 | 9.2 | 6.6 |
| Aromatic Compounds having 8 carbon atoms | 1.4 | 32.1 | 18.5 | 1.4 | 3.2 | 5.6 |
| Aromatic Compounds having 9 carbon atoms | 71.0 | 13.2 | 21.4 | 71.0 | 47.6 | 48.8 |
| Trimethylbenzene | 49.7 | 8.7 | 15.4 | 49.7 | 34.6 | 35.5 |
| Others | 21.3 | 4.4 | 6.0 | 23.1 | 12.9 | 13.3 |
| Aromatic Compounds having 10 or more carbon atoms | 3.0 | 8.2 | 7.7 | 3.0 | 2.5 | 2.6 |
| Total | 100.0 | 100.0 | 100.0 | 100.0 | 100.0 | 100.0 |
| Conversion Ratio of Benzene (% by mass) |  | 41.9 | 36.7 |  | 3.2 | 3.2 |
| Conversion Ratio of C9 AHC (% by mass) |  | 81.5 | 69.8 |  | 33.0 | 31.2 |
| Trimethylbenzene |  | 82.4 | 69.0 |  | 30.3 | 28.6 |
| Others |  | 79.3 | 71.7 |  | 44.2 | 42.4 |
| Variation of Conversion Ratio of Benzene (%) |  |  | 87.4 |  |  | 98.9 |
| Variation of Conversion Ratio of C9 AHC |  |  | 85.7 |  |  | 94.7 |

As shown in the results given in Tables 1 and 2, it can be easily found that the conversion of benzene and aromatic hydrocarbon compounds having 9 or more carbon atoms in the examples were high after 72 hrs. as well as after 360 hrs and thus the catalysts were not so deactivated.

On the other hand, as shown in Table 3, the conversion thereof was lower after 360 hrs with a higher catalyst deactivation in the comparative example 1 wherein the material oil having a boiling point out of the range specified in the present invention was used.

Also, as shown in Table 3, the conversion of aromatic hydrocarbon compounds having 9 or more carbon atoms was lower after 72 hrs. in the comparative example 2 wherein the zeolite having a maximum diameter among diameters of micropores of less than 0.6 nm was used, and the conversion of trimethylbenzene was particularly low. Further, the conversion was particularly lower after 360 hrs. with a larger catalyst deactivation. It can be clearly recognized that the amount of hexane in the prepared oil was smaller in particular and thus fatty hydrocarbon compounds were largely decomposed in the comparative example 3 wherein the same catalyst used in the comparative example 2 and the material oil containing a considerable amount of fatty hydrocarbon compounds having 6 and 7 carbon atoms were used.

In addition, the conversion in the comparative examples 4 and 5 wherein zeolites with a smaller ratio of SiO$_2$/Al$_2$O$_3$ were used were lower with higher catalyst deactivation as shown in Tables 4 and 5. Furthermore, the conversion of benzene and aromatic hydrocarbon compounds having 9 or more carbon atoms was extremely lower in the comparative example 6 wherein catalyst not containing any metal was used.

As discussed and illustrated above, the catalysts according to the present invention are appropriate for converting benzene and aromatic hydrocarbon compounds having 9 or more carbon atoms into toluene and aromatic hydrocarbon compounds having 8 carbon atoms a more useful gasoline base, and they show a higher activity with less catalyst deactivation and extensively higher selectivity.

In addition, according to the method of the present invention it can effectively be carried out to convert benzene and aromatic hydrocarbon compounds having 9 or more carbon atoms into toluene and aromatic hydrocarbon compounds having 8 carbon atoms.

What is claimed is:

1. A method comprising converting benzene and aromatic hydrocarbon compounds having 9 or more carbon atoms contained in a material oil having a boiling point of 30–210° C. into toluene and aromatic hydrocarbon compounds having 8 carbon atoms in the presence of hydrogen and a catalyst being at least one Group VIII or Group VIA metal or compound thereof on a carrier containing zeolites in which the maximum diameter of the zeolite micropores is 0.6–1 nm and the molar ratio of SiO$_2$/Al$_2$O$_3$ is 150 to 250.

2. A method according to claim 1, wherein the maximum diameter of the zeolite micropores is 0.6–0.8 nm, the metal is at least one member selected from the group consisting of Ni and Pd, the zeolite has a counter cation compensating the negative charge of said zeolite and the counter cation is a mixture of 40% to 90% hydrogen ion and 10% to 60% at least one alkali metal ion or alkaline earth metal ion.

3. A method according to claim 1, wherein a sulfurization pre-treated catalyst is employed.

4. A method according to claim 1, wherein said zeolite is at least one member from the group consisting of mordenite and Y zeolite.

5. A method according to claim 1, wherein said zeolite is mordenite.

6. A method according to claim 1, wherein the metal is at least one member selected from the group consisting of Ni, Pd and Ir.

7. A method according to claim 1, wherein the metal is at least one member selected from the group consisting of Ni and Pd.

8. A method according to claim 1, wherein the zeolite has a counter cation compensating the negative charge of said zeolite which is a mixture of hydrogen ion and at least one alkali metal ion or alkaline earth metal ion.

9. A method according to claim 8, wherein the ion equivalent ratio of hydrogen ion to the entire counter cation is 30% or higher.

10. A method according to claim 8, wherein the ion equivalent ratio of hydrogen ion to the entire counter cation is from 40% to 90%.

11. A method according to claim 8, wherein the alkali metal ion is selected from the group consisting of $K^+$, $Na^+$ and a mixture thereof.

12. A method according to claim 8, wherein the ion equivalent ratio of the at least one alkali metal ion or alkaline earth metal ion to the entire counter cation is from 10 to 60%.

13. A method according to claim 1, wherein said material oil has a boiling point of 30~195° C.

14. A method according to claim 1, wherein an amount of benzene in the material oil is 10% by mass or more on the basis of the total amount of the entire material oil.

15. A method according to claim 1, wherein an amount of aromatic hydrocarbon compounds having 9 or more carbon atoms in the material oil is 50% by mass or more on the basis of the total amount of the entire material oil.

16. A method according to claim 1, wherein an amount of aromatic hydrocarbon compounds having 9 carbon atoms in the material oil is 50% by mass or more on the basis of the total amount of the entire material oil.

17. A method according to claim 1, wherein the ratio between benzene and aromatic hydrocarbon compounds having 9 or more carbon atoms in the material oil is 1–5.

* * * * *